(12) United States Patent
Lordo

(10) Patent No.: US 7,931,144 B2
(45) Date of Patent: *Apr. 26, 2011

(54) PATIENT INTERFACE PACKAGING WITH INTEGRATED SIZING GAGE

(75) Inventor: Richard Joseph Lordo, Butler, PA (US)

(73) Assignee: RIC Investments LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/783,004

(22) Filed: May 19, 2010

(65) Prior Publication Data

US 2010/0230314 A1   Sep. 16, 2010

Related U.S. Application Data

(63) Continuation of application No. 10/986,693, filed on Nov. 12, 2004, now Pat. No. 7,743,920, which is a continuation-in-part of application No. 10/251,069, filed on Sep. 20, 2002, now abandoned.

(60) Provisional application No. 60/328,261, filed on Oct. 10, 2001.

(51) Int. Cl.
  *B65D 85/00* (2006.01)
  *B65D 77/00* (2006.01)
(52) U.S. Cl. ............... 206/438; 206/459.5; 206/278
(58) Field of Classification Search ............ 206/438, 206/278, 363, 554, 459.5, 459.1, 806, 292; 383/10, 11, 8, 9
See application file for complete search history.

(56) References Cited

U.S. PATENT DOCUMENTS

| | | | |
|---|---|---|---|
| 2,752,689 A * | 7/1956 | Adams et al. .......... 33/513 |
| 2,893,546 A | 7/1959 | Kendell |
| 3,116,829 A | 1/1964 | Pacelli |
| 3,220,543 A | 11/1965 | McCord |
| 3,306,492 A * | 2/1967 | Kugler ............... 221/63 |
| 3,655,036 A * | 4/1972 | Corelli et al. ......... 206/526 |
| 4,269,315 A * | 5/1981 | Boyce ............... 206/438 |
| 4,453,629 A * | 6/1984 | Goldberg ............ 206/457 |
| 4,485,921 A | 12/1984 | Geller |
| 4,653,642 A | 3/1987 | Hakun |
| 5,615,767 A | 4/1997 | Eull |
| 5,709,204 A | 1/1998 | Lester |
| 5,819,939 A * | 10/1998 | Boyer ............... 206/461 |
| 5,921,239 A | 7/1999 | McCall |
| 6,079,877 A * | 6/2000 | Chew ................ 383/8 |
| 6,116,424 A * | 9/2000 | Leu ................ 206/554 |
| 6,478,146 B1 | 11/2002 | Chapman |
| 6,536,951 B1 | 3/2003 | Sill |
| 6,571,797 B1 | 6/2003 | Magidson |
| 6,601,705 B2 | 8/2003 | Molina |
| 2001/0029952 A1 | 10/2001 | Curran |
| 2003/0000862 A1* | 1/2003 | Matushek ........... 206/459.5 |

FOREIGN PATENT DOCUMENTS

EP         305236 A1 *  3/1989

* cited by examiner

*Primary Examiner* — Steven A. Reynolds
(74) *Attorney, Agent, or Firm* — Michael W. Haas

(57) ABSTRACT

A patient interface packaging that includes an integrated sizing template. The packaging system includes a container having an inner chamber containing a patient interface device having a size contained within. The packaging further includes an outer exterior having an integral flap. The integral flap includes at least one opening therethrough forming a sizing template. The size of the opening corresponds to the size of the mask contained within the package so that the opening may be fitted to the nose region of a patient's to allow the user to determine an appropriate size patient interface device that matches his or her anatomical dimensions.

17 Claims, 5 Drawing Sheets

US 7,931,144 B2

PATIENT INTERFACE PACKAGING WITH INTEGRATED SIZING GAGE

CROSS-REFERENCE TO RELATED APPLICATIONS

This application is a Continuation under 35 U.S.C. §120/121 from U.S. patent application Ser. No. 10/986,693, filed Nov. 12, 2004, now U.S. Pat. No. 7,743,920, which is a Continuation-in-Part of and which claims priority under 35 U.S.C. §120/121 from U.S. patent application Ser. No. 10/251,069, filed Sep. 20, 2002 now abandoned, which claims priority under 35 U.S.C. §119(e) from provisional U.S. patent application No. 60/328,261 filed Oct. 10, 2001 the contents of which are incorporated herein by reference.

BACKGROUND OF THE INVENTION

1. Field of the Invention

The present invention pertains to a packaging system for a patient interface device, such as a respiratory mask, and, in particular, to a packaging system where the packaging containing the respiratory mask includes an integrated sizing gage for use in determining whether the mask contained in that package is a proper fit for a user.

2. Description of the Related Art

A variety of respiratory masks or patient interface devices are known that have flexible seals and cover the nose, mouth, or both of a human user and are designed to create a seal against the user's face. Because of the sealing effect that is created, gases can be provided at a positive pressure within the mask for consumption by the user. Uses for such masks range from high altitude breathing, i.e. aviation applications, to mining and fire fighting applications, to various medical diagnostic and therapeutic applications. For example, such masks are used to delivery continuous positive airway pressure (CPAP) or variable airway pressure, which varies with the patient's respiratory cycle, to an airway of a patient. This is done to treat a medical disorder, such as sleep apnea syndrome, in particular, obstructive sleep apnea (OSA), or congestive heart failure or to ventilate a patient who has a compromised respiratory ability.

A requisite of such respiratory masks is that they provide an effective seal against the user's face to prevent leakage of the gas being supplied. Commonly, in prior mask configurations, a good mask-to-face seal has been attained in many instances only with considerable discomfort to the user. This problem is most crucial because such masks are typically worn for an extended period of time. One concern in such a situation is that a user may avoid wearing an uncomfortable mask, defeating the purpose of the prescribed pressure support therapy.

Thus, to ensure a comfortable fit providing an adequate seal, it is important that the mask fit a patient's face properly. Typically, respiratory masks are provided in a range of sizes, such as "small", "medium" and "large", or "adult" and "child". Traditionally, the product's manufacture supplies a sizing gage, also referred to as a template, for use in determining which size is best suited for each user. The sizing template is typically formed from a rigid material with a plurality of cutouts, each cutout corresponding to a different size of the mask. The user places the template on the part of the body to be measured, such as over the nose and/or mouth, to determine which the size mask best fits their anatomical features. The user can test their anatomical features in each different size cutout determine which cutout, and, hence, which size mask, best matches their features.

This template must be available to the provider each time a patient is sized. A disadvantage to this system is the provider must remember to take a sizing gage with them to a patient's residence, in the case of a homecare application, or to the patient's bedside, in the case of a hospital application. It should be apparent that one disadvantage, is that this rigid gage may not always be available.

In another sizing technique, "eyeballing" is used. In this instance, the provider will guess the appropriate size product for the patient. It should be apparent that this method can easily result in the selection of the wrong product size. In another sizing procedure, the mask packaging is opened and the product is tried on the patient. If the mask is not the correct size, the mask must be cleaned and disinfected prior to use on the next patient, or the mask may be disposed. Disposing of unused product is obviously wasteful and not profitable. Cleaning and/or disinfecting product is time consuming and may require special equipment or chemicals to properly clean the product.

Thus, an advantage exists to provide a sizing gage with every product, eliminating the need to carry a durable gage or many different gages to suit the broad range of products available. Guessing at mask sizes would also be eliminated, as a sizing gage would be readily available. Providers would no longer be required to open products that would ultimately not be used on the patient. The potential disposal of unused product and the need for disinfection equipment and chemicals would be eliminated.

SUMMARY OF THE INVENTION

Accordingly, it is an advantage of the present invention to provide a sizing gage that addresses the above-identified concerns and that overcomes the shortcomings of conventional sizing systems. This advantage is achieved according to the present invention by providing a patient interface packaging that includes an integrated sizing template. The packaging system of the present invention includes a container having an inner chamber that contains the patient interface device of a particular size. The packaging system also optionally includes a headgear or other accessories for use with the patient interface device and instructions sealed within the container. The packaging further includes an outer exterior having an integral flap. The integral flap includes at least one opening therethrough. One of the openings corresponds to the size of the patient interface device sealed within the packaging, such that the opening may be fitted to the anatomical region of the patient to which the patient interface is applied. For example, if the patient interface is a nasal mask, the opening may be triangular shaped so that the user applies the opening to the nose to determine if that sized opening, and, thus, the mask contained within the packaging is a proper fit. In an alternate embodiment, the flap includes at least one three-dimensional profile of an anatomical region, such as a nose, corresponding to the size of a patient interface device. It is to be understood, however, that the present invention contemplates providing any one of a variety of types of sizing gauges on the patient interface packaging.

These and other features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

Figure 1A:
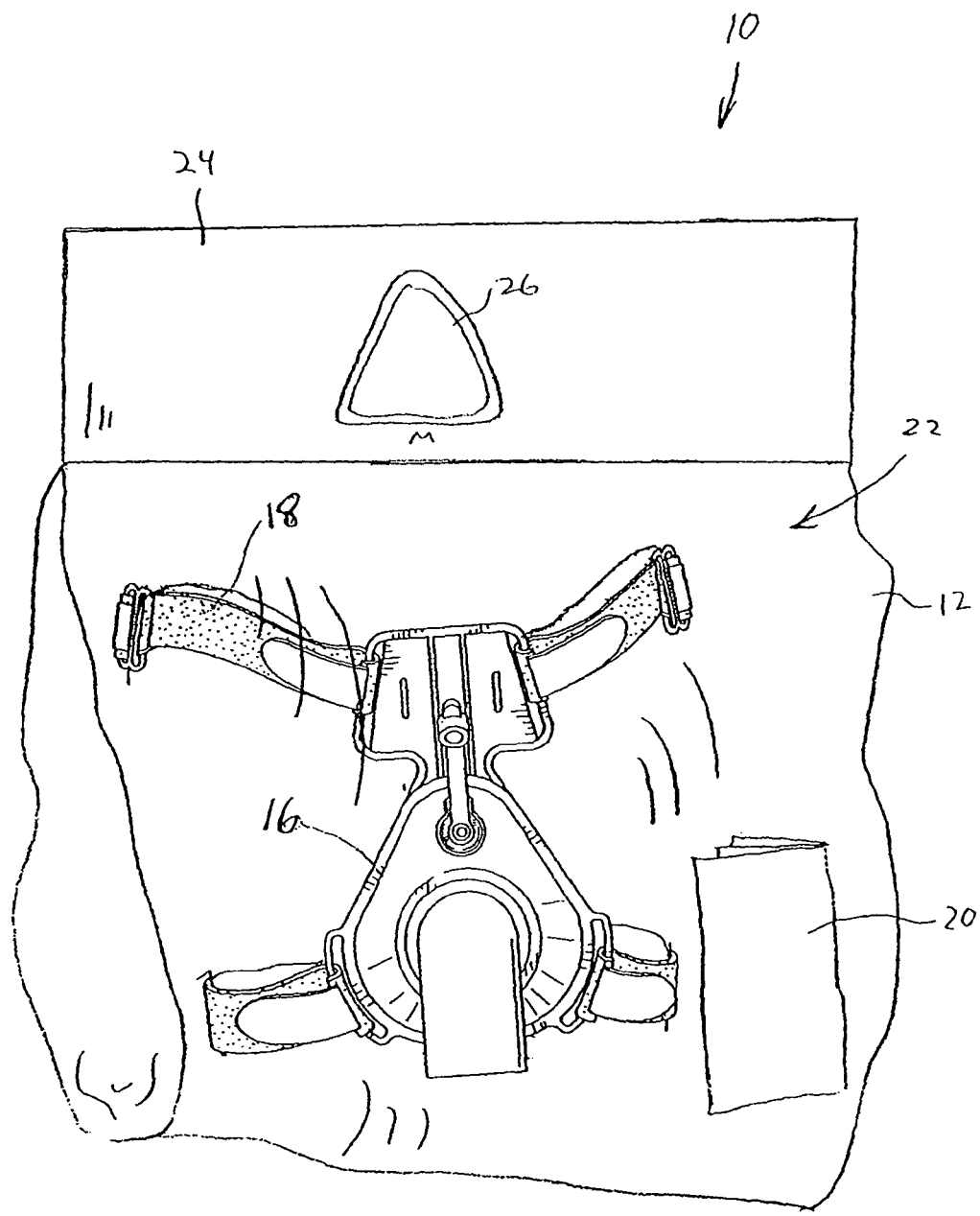
FIGS. 1A and 1B are perspective views of a packaging system according to a first embodiment of the present invention.

FIG. 1A illustrates exemplary embodiments of a packaging system 10 according the principles of the present invention. Packaging system 10 of this first exemplary embodiment includes a container or bag 12, preferably formed from a clear, see-through material so that the contents of the container can be viewed. It is to be understood, however, that the present invention contemplates forming container 12 from any suitable material.

Container 12 includes an inner chamber 14 containing a patient interface device 16, which in the illustrated embodiment is a respiratory mask. Interface device 16 has a particular size, such as small, medium or large, which each size being suited to fit a population of patient having anatomical features of a corresponding size. In the illustrated exemplary embodiment, container 12 also includes a headgear 18, and instructions 20 sealed within. It is can be appreciated that the headgear and instructions are optional accessories and need not be included in the container.

Container 12 further includes an outer exterior 22 having an integral flap 24. In a presently preferred embodiment, flap 24 is formed from the same material as container 12. However, the present invention contemplates that the flap and the container need not be formed from the same material. Integral flap 24 includes an opening 26 therethrough forming a sizing template so that the combination of the integral flap an opening define a sizing gage that is affixed to the container containing the object to which the sizing gas applies. That is, openings 26 has a size that corresponds to the size of the mask 16 sealed within container 12, so that opening 26 may be fitted to the corresponding portion of the patient's face to determine if mask 16 in container 12 is the appropriate size for the patient.

Figure 1B:
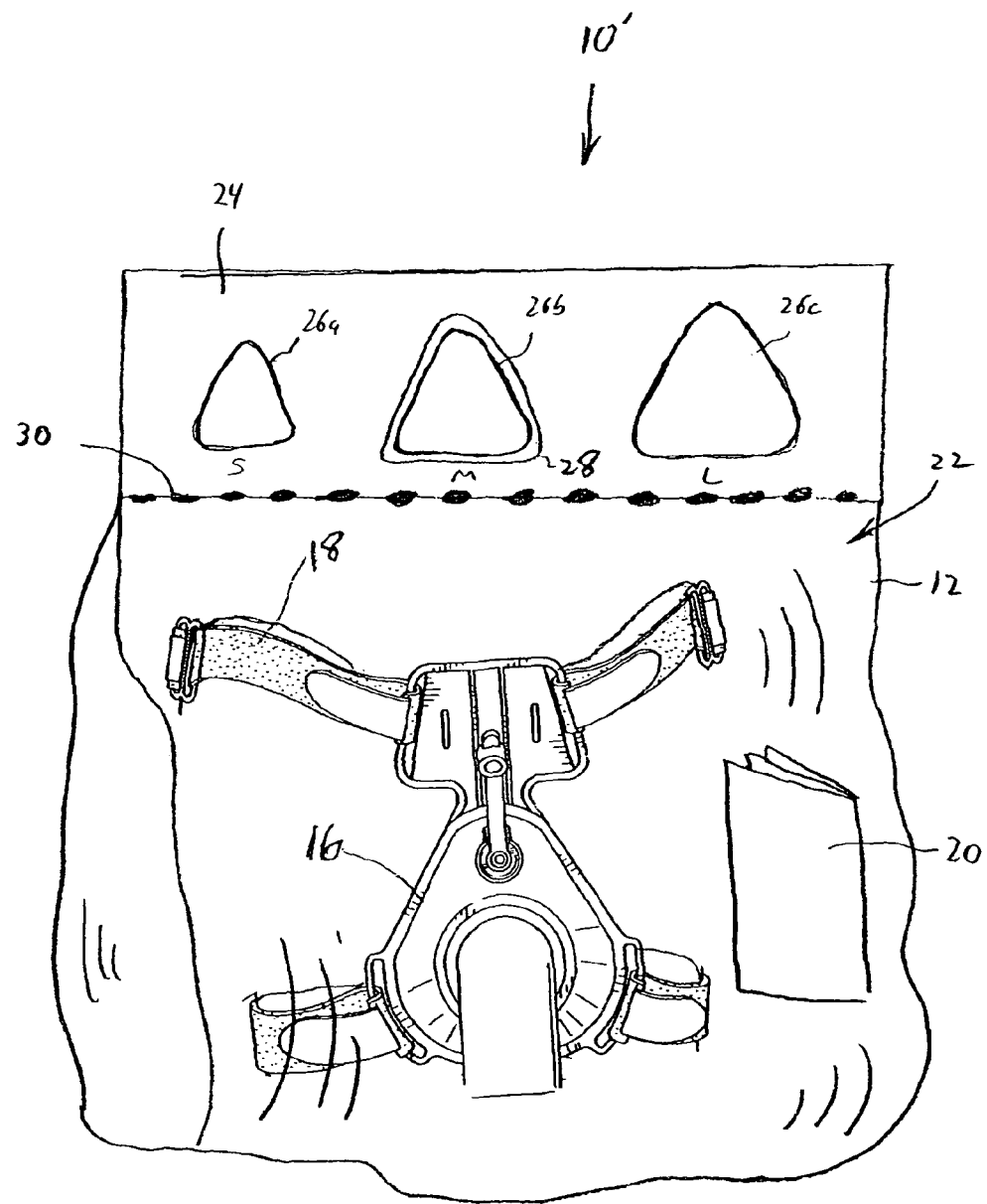

FIG. 1B illustrates a packaging system 10' similar to packaging system 10 of FIG. 1A. However, in the embodiment shown in FIG. 1B, a plurality of openings 26a, 26b, and 26c are provided on integral flap 24. One of the openings 26a, 26b, or 26c has a size that corresponds to the size of the patient interface device contained within the packaging. The other openings have sizes that correspond to other size patient interface devices. This configuration for a sizing gage formed from integral flap 24 and opening 26a-26c, makes it is possible for a user to determine the appropriate mask size from a family of mask sizes for a particular patient from a single flap.

In the packaging system shown in FIG. 1A, the user must have available three packages, each containing the three different sized masks for the family of masks (small, medium and large, for example) so that the user can test each size opening, via the integral sizing gage, to determine which size mask fits best. In the packaging system shown in FIG. 1B, on the other hand, the different masks sizes for the family of similar masks are all represented by the openings provided on a single integral flap. Thus, the user need only have available one packaging system in order to test each different size template to determine which size mask fits best.

As shown in FIG. 1B, integral flap 24 is illustrated having three triangular-shaped openings 26a-26c corresponding to three different masks sizes. It can be appreciated that there may be some confusion as to which size mask is contained in the packaging, unlike the embodiment shown in FIG. 1A, where there is only one opening and only one mask of corresponding size contained in the packaging. For this reason, it is preferable for the size opening 26a, 26b or 26c that corresponds to the size of the mask contained within the packaging to be set off from the other openings by an indicia, such as a darkened outline 28. For example, if mask 18 in packaging system 10' is a medium sized mask, opening 26b, which corresponds to the medium size mask, includes an indicate in the form of darkened outline 28 that highlights to the user that the mask contained in the packing has a size that corresponds to opening 26b.

It can be appreciated that there is an almost infinite number of different ways to highlight which opening has a size that corresponds to the size of the mask contained in the packaging system. For example, a color code scheme can be used or the opening that has a size that corresponds to the size of the mask contained in the packaging system may be set apart from the other opening, and may even be provided on a second, separate flap, that is also integral with container 12.

Although exemplary embodiments have been described above, it is to be understood the present invention can vary from that shown and described. The present invention contemplates the packaging material does not have to be see-through or may only have a portion which is see-through and may be formed from another material such as paper. Further, the flap may be stiffened with an additional material, such as cardboard, and/or may be separated from the rest of the outer exterior of the packaging by perforations 30, as shown in FIG. 1B. Also, it should be appreciated the contents of the package can vary.

Figure 2A:
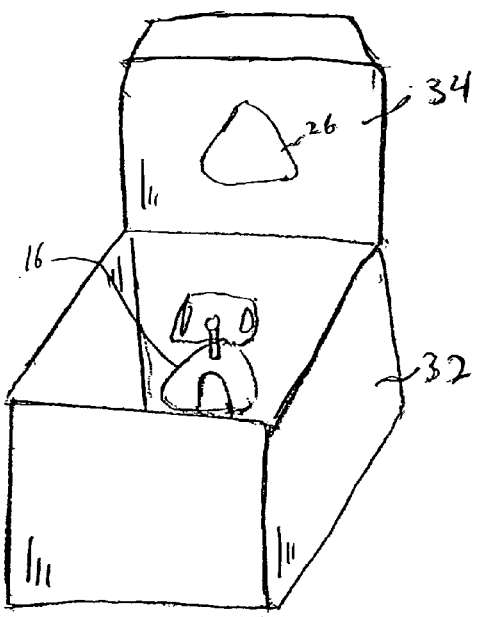
FIGS. 2A-2D are perspective views of a packaging system according to an alternative embodiment of the present invention.
Figure 2B:
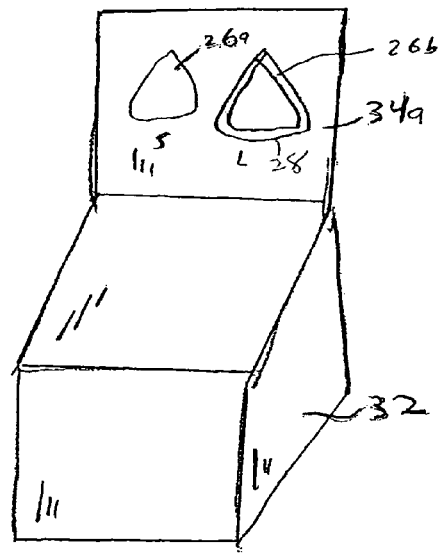
Figure 2C:
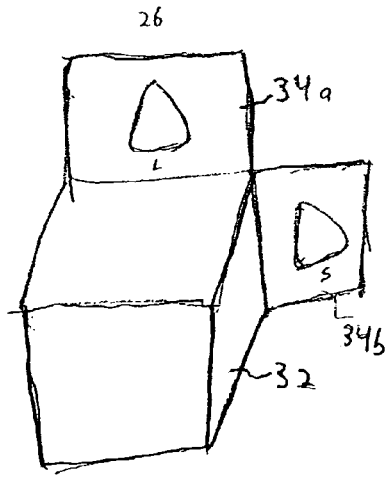
Figure 2D:
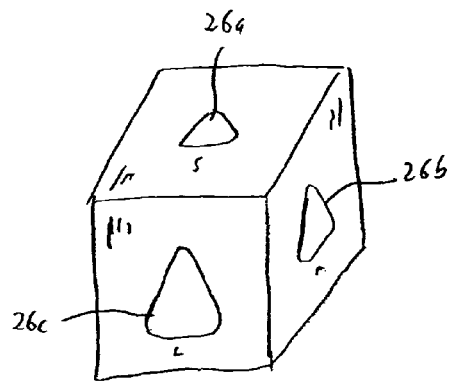

A packaging system according to an alternative embodiment of the present invention is illustrated in FIGS. 2A-2C. In this alternate embodiment, the packaging system includes a relatively rigid container 32, such as a box, having at least one integral flap 34. The box defines a compartment that contains at least one patient interface device 16, such as a mask, having a size. The box flap includes at least one opening 26 having a size that corresponds to the size of the mask contained within the box. Additional openings may be provided as discussed above. The box flap containing the template opening may be a side of the box or a box lid, as illustrated in FIG. 2A. The present invention also contemplates that container 32 include an additional integral flap 34a that protrudes from the container and does not define a side of the container. FIG. 2B illustrates a single flap 34a, and FIG. 2C illustrates multiple flaps 34a and 34b that function as sizing gages. As discussed above, each integral flap, can include one or more sizing templates (openings). FIG. 2D illustrates yet another embodiment where the sizing templates or opening 26 are provided on different sizes of the container 32.

As noted above, where more than one sizing template is provided on a container, it is preferable to provide some sort of indication as to which template corresponds to the patient interface device contained in the box. Of course, the box or product inside the box can be labeled by size, so that once the user determines which size mask he needs using the integrated sizing gage, he merely has to select the package indicated as containing that size mask. In which case, there need be no indicia that highlights the template that corresponds to the mask in the box. Rather, the box or product in the box is marked with its size and the user refers to this marking in selecting the proper product, which relying on indicia provided on the on the template to indicate the size of the product contained in the packaging.

Figure 3A:
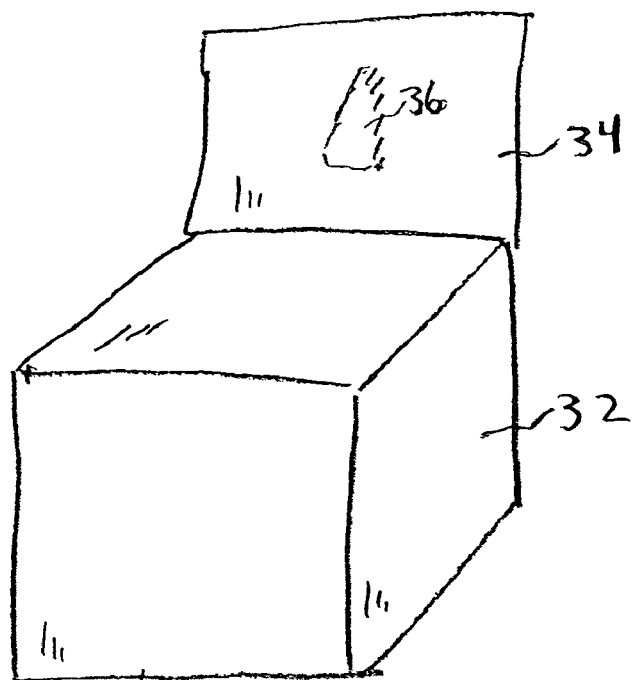
FIGS. 3A and 3B are perspective and side views, respectively, of yet another alternate embodiment of the packaging system according to the principles of the present invention.
Figure 3B:
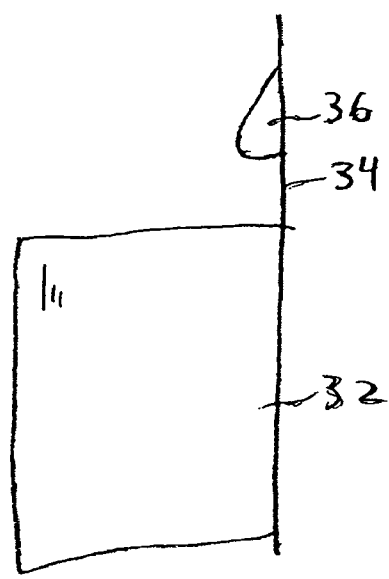

In an additional alternative embodiment illustrated in FIGS. 3A and 3B. Instead of an opening, integral flap 34 includes at least one three-dimensional profile 36 of an anatomical feature, such as the nose, corresponding to a mask size. Profile 36 is structured to receive the nose of a patient to determine the proper size mask for that patient. Integral flap 36 having three-dimensional profile 36 is preferable formed from a plastic material and then heat-sealed to container 32. The present invention, also contemplates providing this three-dimensional profile in the side of the box, similar to that shown in FIG. 2D, so that there is no opening on the side of the box.

Figure 4A:
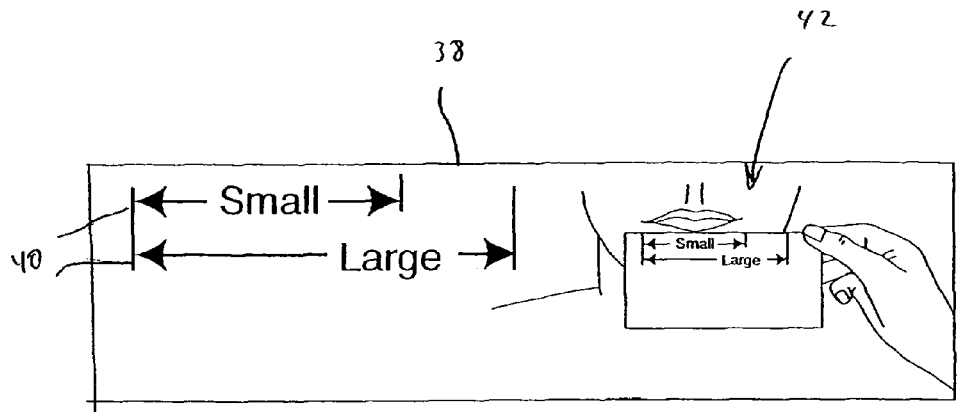
FIGS. 4A and 4B are front views of a sizing gage according to another embodiment of the present invention.
Figure 4B:
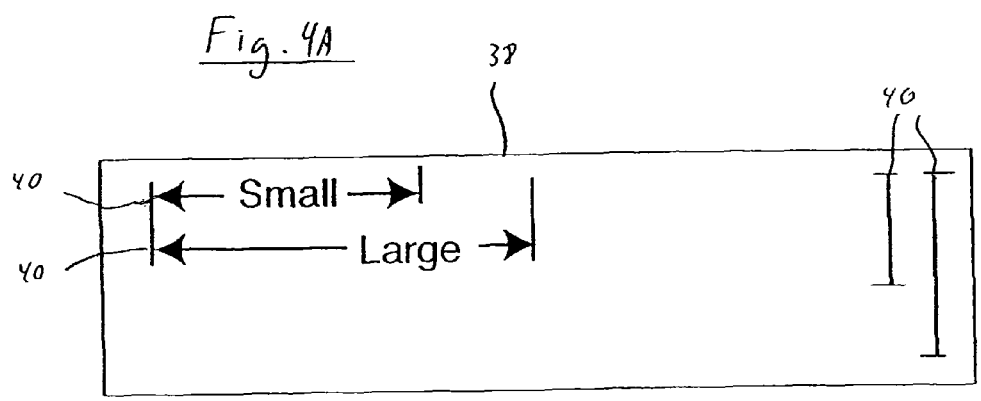

Yet another embodiment of the present invention is shown in FIGS. 4A and 4B, which illustrates only the flap and omits the container to which the flap is integrally attached. As shown on FIGS. 4A and 4B, sizing template or integral flap 38 includes sizing lines 40 rather than openings or contoured profiles. Sizing lines 40 correspond to specific dimensions of an anatomical feature, such as the width of a closed mouth or the distance from the nasion to the sublabiale, which is the region of the face between the lower lip and chin. In addition to sizing lines 40, integral flap 38 further includes an illustration 42 of how the sizing lines 40 should be lined up to a patient's face. In the embodiment illustrated in FIG. 4A, a depiction 42 of a sizing template being held up to the appropriate area of a patient's face, in this case a closed mouth, is illustrated on the sizing template itself. This depiction provides a guide for the provider as to how to use the template.

As shown in FIG. 4B, the present invention contemplates that the integral flap can include multiple sets of sizing templates. This may necessary depending on the manner in which the patient interface device is sized.

Figure 5:
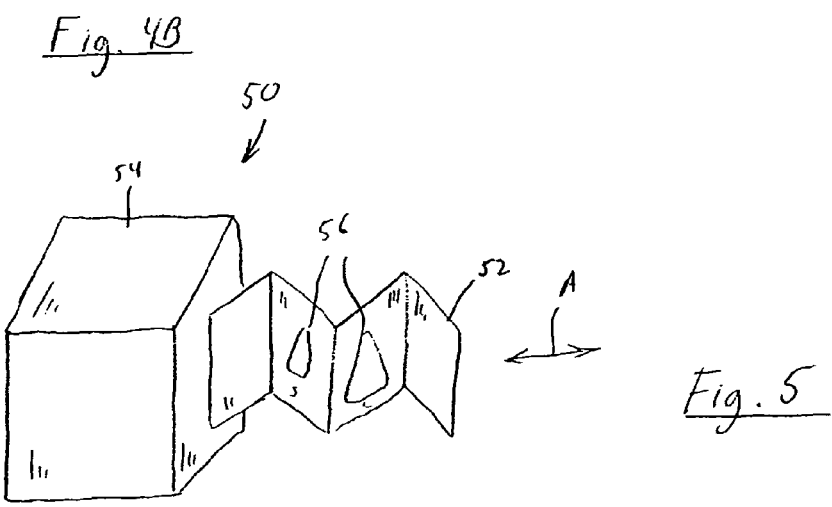
FIG. 5 is a perspective view of still another embodiment of a packaging system according to the principles of the present invention.

FIG. 5 illustrates a further embodiment of a packaging system 50 according to the principles of the present invention. In this embodiment, an integral flap 52 is attached to a surface of a container 54. Flap 52 is extendable from container 54 in an accordion-like fashion, as indicated by arrow A. One or more openings 56 are provided in extendable, integral flap 52 in the same manner discussed above. Preferably, flap 52 includes a fastening structure, such as an adhesive or hook and loop structure, that allows the flaps to be folded and stored against the side of container 54.

While FIG. 5 illustrates flap 52 as being attached to an exposed surface of container 54, it is to be understood that the present invention contemplates attaching the flap to other structures of the packaging. For example, flap 52 can be attached on the inside surface of the lid that closes container 54. In which case, the user merely opens the lid and unfolds the flap to access the sizing gage. If desired, barriers of separate packaging for the product in the container can be provided to prevent direct access to the product while the lid is open.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A respiratory mask packaging system comprising:
a container having an inner chamber sized to hold only one of a first sized respiratory mask and a second sized respiratory mask at a time, the second sized respiratory mask being larger than the first sized respiratory mask; and
a sizing gage integral with the container, the sizing gage having a first substantially triangular-shaped opening corresponding to the first sized respiratory mask and a second substantially triangular-shaped opening that is larger than the first substantially triangular-shaped opening and that corresponds to the second sized respiratory mask, wherein only one of the first substantially triangular-shaped opening and the second substantially triangular-shaped opening has an indicia associated therewith which indicates which one of the first sized respiratory mask and the second sized respiratory mask is held within the inner chamber, and wherein the sizing gage is spaced from and non-coaxial with the one of the first sized respiratory mask and the second sized respiratory mask that is held within the inner chamber.

2. The respiratory mask packaging system according to claim 1, wherein each of the first and second triangular-shaped openings is adapted to receive the nose of a user such that the fit of one of the first sized respiratory mask and the second sized respiratory mask can determined.

3. The respiratory mask packaging system according to claim 1, wherein the container is rigid.

4. The respiratory mask packaging system according to claim 1, further comprising at least one sizing line separate from the sizing gage.

5. The respiratory mask packaging system according to claim 4, further comprising an illustration of how the at least one sizing line should be lined up to a user's face.

6. The respiratory mask packaging system of claim 1, wherein:
the first substantially triangular-shaped opening comprises a small substantially triangular-shaped opening corresponding to a small sized respiratory mask;
the second substantially triangular-shaped opening comprises a medium substantially triangular-shaped opening corresponding to a medium sized respiratory mask; and
the sizing gage further comprises a large substantially triangular-shaped opening corresponding to a large sized respiratory mask, wherein the large sized respiratory mask is larger than the medium sized respiratory mask and the small sized respiratory mask, wherein the inner chamber sized to hold only one of the small sized respiratory mask, the medium sized respiratory mask and the large sized respiratory mask at a time, wherein large substantially triangular-shaped opening is larger than small substantially triangular-shaped opening and the medium substantially triangular-shaped opening, and wherein only one of the small substantially triangular-shaped opening, the medium substantially triangular-shaped opening and the large substantially triangular-shaped opening has an indicia associated therewith which indicates which one of small sized respiratory mask, the medium sized respiratory mask and the large sized respiratory mask is held within the inner chamber.

7. The respiratory mask packaging system of claim 1, wherein the container is a bag.

8. The respiratory mask packaging system of claim 1, wherein the container comprises a flap, and wherein the sizing gage is on the flap.

9. The respiratory mask packaging system of claim 1, wherein the openings do not open into the inner chamber.

10. An assembly comprising:
   a container having an inner chamber configured and sized to hold only a single respiratory mask at a time therein;
   a respiratory mask disposed in the inner chamber, the respiratory mask being structured to accommodate a nose, and the respiratory mask having a particular size; and
   a nose sizing gage comprising a substantially triangular-shaped opening provided in a planar surface of either the container or a flap attached to the container, the substantially triangular-shaped opening being defined by a first edge portion, a second edge portion and a third edge portion of the planar surface, the substantially triangular-shaped opening having a predetermined size that is based upon and corresponds to the particular size of the respiratory mask such that the substantially triangular-shaped opening may be fitted to a patient's nose to determine if the particular size of the respiratory mask is appropriate for the patient.

11. The assembly of claim 10, wherein the opening is spaced from and non-coaxial with the respiratory mask.

12. The assembly of claim 10, wherein:
   the substantially triangular-shaped opening comprises a first substantially triangular-shaped opening;
   the respiratory mask comprises a first respiratory mask; and
   the assembly further comprises a second substantially triangular-shaped opening provided in the planar surface, a second planar surface of the container or a second flap attached to the container, the second substantially triangular-shaped opening having a different predetermined size than the first substantially triangular-shaped opening and corresponding to a second respiratory mask having a different particular size than the first respiratory mask, wherein the different predetermined size is based upon and corresponds to the different particular size of the second respiratory mask such that the second substantially triangular-shaped opening may be fitted to a patient's nose to determine if the different particular size of the second respiratory mask is appropriate for the patient.

13. The assembly of claim 12, wherein the first substantially triangular-shaped opening has an indicia associated therewith which indicates that the first respiratory mask is held within the inner chamber.

14. The assembly of claim 10, wherein the substantially triangular-shaped opening does not open into the inner chamber.

15. The assembly of claim 10, wherein the substantially triangular-shaped opening is provided in the container.

16. The assembly of claim 10, wherein the substantially triangular-shaped opening is provided in the flap.

17. The assembly of claim 10, wherein:
   the container comprises a bag and the flap is connected to the bag;
   an inside of the bag forms the inner chamber; and
      the substantially triangular-shaped opening is provided in the flap.

\* \* \* \* \*